(12) United States Patent
Hashim et al.

(10) Patent No.: US 7,807,718 B2
(45) Date of Patent: Oct. 5, 2010

(54) GLYCERIDE ESTERS FOR THE TREATMENT OF DISEASES ASSOCIATED WITH REDUCED NEURONAL METABOLISM OF GLUCOSE

(75) Inventors: Sami A. Hashim, 42 S. Lawn Ave., Dobbs Ferry, NY (US) 10522; Joanna Jusis, Lincoln Park, NJ (US); Jenifer Heydinger Galante, Oakland, NJ (US); Joseph C. Rongione, Middletown, NJ (US)

(73) Assignee: Sami A. Hashim, Dobbs Ferry, NY (US)

( * ) Notice: Subject to any disclaimer, the term of this patent is extended or adjusted under 35 U.S.C. 154(b) by 0 days.

(21) Appl. No.: 12/304,341

(22) PCT Filed: Jun. 29, 2007

(86) PCT No.: PCT/US2007/072441

§ 371 (c)(1),
(2), (4) Date: Apr. 6, 2009

(87) PCT Pub. No.: WO2008/005818

PCT Pub. Date: Jan. 10, 2008

(65) Prior Publication Data

US 2009/0197952 A1   Aug. 6, 2009

Related U.S. Application Data

(60) Provisional application No. 60/818,115, filed on Jun. 30, 2006.

(51) Int. Cl.
*A01N 37/02* (2006.01)
(52) U.S. Cl. ...................... 514/552; 514/546
(58) Field of Classification Search .................. 514/547, 514/552
See application file for complete search history.

(56) References Cited

U.S. PATENT DOCUMENTS

| 5,093,044 | A * | 3/1992 | Wretlind et al. ............. 514/547 |
| 6,207,856 | B1 | 3/2001 | Veech |
| 6,323,237 | B1 | 11/2001 | Veech |
| 6,380,244 | B2 | 4/2002 | Martin et al. |
| 6,835,750 | B1 | 12/2004 | Henderson |
| 7,351,736 | B2 | 4/2008 | Veech |
| 2004/0171671 | A1* | 9/2004 | Veech ........................ 514/450 |
| 2006/0115880 | A1 | 6/2006 | Ghoul et al. |
| 2006/0280721 | A1 | 12/2006 | Veech et al. |

FOREIGN PATENT DOCUMENTS

| WO | WO 95/09144 | 4/1995 |
| WO | WO 95/09146 | 4/1996 |

OTHER PUBLICATIONS

Treatment of Parkinson disease with diet-induced hyperketonemia: A feasibility study; Neurology, 64:728-730; (1 pg), 2005.
Intravenous Feeding of the Rat with Short Chain Fatty acid Esters, II. Monacetoacetin; (2 pages), 1978.
Monoglyceryl Acetoacetate: A Ketone Body-carbohydrate Substrate For Parenteral Feeding of the Rat; J. Nult. 109: 1168-1174 (1979) (7 pages).
A Ketogenic diet as a potential novel therapeutic intervention in amyotrophic lateral sclerosis; BMC Neuroscience (2006)7:29 (6 pages).

* cited by examiner

*Primary Examiner*—Deborah D Carr
(74) *Attorney, Agent, or Firm*—Cowan, Liebowitz & Latman, P.C.; Mark Montague, Esq.

(57) ABSTRACT

Provided are alternative sources of ketone bodies for reducing or eliminating symptoms of Parkinson's disease, amyotrophic lateral sclerosis (ALS, also called Lou Gehrig's disease), Alzheimer's disease, Huntington's disease, epilepsy and other diseases or disorders characterized by impaired glucose metabolism. The alternative sources of ketone bodies include mono-, di- and triglyceride esters of acetoacetate and mixtures thereof, and/or mono-, di- and triglyceride esters of 3-hydroxybutyrate and mixtures thereof. These glyceride esters can be administered orally as a dietary supplement or in a nutritional composition.

12 Claims, No Drawings

GLYCERIDE ESTERS FOR THE TREATMENT OF DISEASES ASSOCIATED WITH REDUCED NEURONAL METABOLISM OF GLUCOSE

RELATED APPLICATIONS

This application claims priority to U.S. provisional patent application Ser. No. 60/818,115, filed Jun. 30, 2006. The entire specification and all of the claims of the provisional application referred to above are hereby incorporated by reference to provide continuity of disclosure.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

This invention generally relates to the field of therapeutic agents useful in the treatment of Parkinson's disease and other diseases associated with reduced neuronal metabolism of glucose, including for example, Alzheimer's disease, amyotrophic lateral sclerosis (ALS, also called Lou Gehrig's disease), Huntington's disease, and epilepsy.

Diseases such as Parkinson's disease are marked by a reduced ability of neuronal cells to metabolize glucose as an energy source. It has been demonstrated that ketone bodies (acetoacetate and 3-hydroxybutyrate) serve as alternate energy sources for the brain when glucose supplies are limited. Ketone bodies formed by the body through use of a ketogenic diet have been shown to alleviate symptoms of Parkinson's disease in humans. However, ketone bodies cannot be provided directly to the human body in an acid form because a metabolic acid imbalance can result. Likewise, if such ketone bodies are provided in their salt form (e.g., Na or K salt forms), a salt electrolytic imbalance can result due to the excess quantities of such ketone bodies used to produce the desired effect. Further, the ketogenic diet is difficult to maintain for a prolonged period of time, as the diet is severely restricted to low-carbohydrate, low-protein, high fat foods.

In general, ketone bodies are normal components of blood plasma. They can be produced in the liver from the metabolism (oxidation) of fatty acids when low amounts of carbohydrates are available. Acetoacetate is one of the two main ketone bodies produced by the human body, the other is 3-hydroxybutyrate (3HB). Acetoacetate can also be reduced in the mitochondria of cells to form 3HB. Once these types of ketone bodies are produced, they can be transported to peripheral tissues (heart, skeletal muscle, kidney, etc.) for use as an energy source. In particular, the brain utilizes ketone bodies when sufficient glucose is not available for energy.

Moreover, ketone bodies are typically produced in small quantities, and because they are rapidly utilized, their concentration in the blood is normally very low. In a healthy human subject, the level of ketone bodies is normally 0.1 mM or less after the consumption of a food source. Blood ketone body concentrations rise where a low carbohydrate diet is utilized, during periods of fasting, or under conditions where glucose may be lowered such as diabetes, for example. Upon overnight fasting, the levels of ketone bodies in a healthy human subject can typically rise to about 0.3 mM. After a three day fast, the level can rise to about 3.0 mM; the levels can climb to about 7 mM after a 24 day fast. (Fenselau, 1981). It has been determined that the maximum capacity for generating ketone bodies (ketogenesis) of the human liver is about 130 g/day. Owen O E, Reichard G A J, Human forearm metabolism during progressive starvation, *J. Clin. Invest.*, 50:1538-1545 (1971). In cases of prolonged starvation, acetoacetate can provide more than 70% of the brain's energy requirements without cellular damage.

Additionally, a ketogenic diet has been successfully used since the 1920's to treat both children and adults with medication-resistant seizure disorders. The diet is based on the brain's ability to utilize ketones as an energy source by mimicking the metabolic effects of fasting while food is being consumed. By eating a high-fat, low-carbohydrate, and low-protein diet, blood ketone levels can be increased and maintained at therapeutic concentrations of 2-8 mmol/L. Such levels are well below the dangerous levels observed in uncontrolled diabetes. Further, such an outcome illustrates that the ketogenic diet treatment can increase blood ketone concentrations to a therapeutically significant level, while avoiding toxicity.

The ketogenic diet, however, is difficult to maintain for a prolonged time. The diet is severely restrictive, and the high fat levels it contains may lead to an undesirable increase in serum low-density lipoprotein (LDL) cholesterol levels and other potentially atherogenic serum lipids. VanItallie et al., Treatment of Parkinson disease with diet-induced hyperketonemia: A feasibility study, *Neurology*, 64:728-730 (2005).

As an alternative, medium chain triglycerides have been used as part of a ketogenic diet since they are readily metabolized to form ketone bodies. U.S. Pat. No. 6,835,750 (Henderson) proposes the use of medium chain triglycerides to produce ketone bodies upon oxidation to treat conditions marked by impaired glucose metabolism in the brain, such as Alzheimer's disease.

Zhao et al (2006) appeared to describe that a ketogenic diet has the potential to alleviate symptoms of amyotrophic lateral sclerosis (ALS or Lou Gehrig's disease) in test animals. Zhao et al., A ketogenic diet as a potential novel therapeutic intervention in amyotrophic lateral sclerosis, *BMC Neuroscience*, 7:29 (2006).

A human clinical trial by VanItallie et al (2005) appeared to observe and describe the potential for a ketogenic diet to alleviate the symptoms of Parkinson's disease. *Neurology*, 64:728-730. However, because the diet is so restrictive and therefore difficult to maintain, the number of test subjects was limited.

It would therefore be desirable to directly provide ketone bodies as an energy source to humans or animals, especially those suffering from conditions involving reduced neuronal glucose metabolism. It is difficult to administer the free acid forms of ketone bodies in humans, as this can induce metabolic acidosis. Use of the sodium salts is also not desirable, as sodium ion overload will occur at the amount of ketone bodies needed to achieve desired plasma concentrations.

The glycerol esters of acetoacetate and 3-hydroxybutyrate have been used to provide ketone bodies for their protein-sparing function. It has been reported in the following references that sufficient levels of ketone bodies in the body could be achieved without detrimental side effects.

For example, studies by Birkhahn and Border demonstrated that monoacetoacetin (the ester corresponding to 1 mole of glycerin and 1 mole of acetoacetate) could be safely infused into rats at the rate of up to at least 50 g/kg body weight/day, a level providing the equivalent of 2/3 the rat's daily caloric requirement. *Amer. J. Clinical Nutrition* 31:436-441, Intravenous Feeding Of The Rat With Short Chain Fatty Acid Esters. II. Monoacetoacetin (1978); *J. Nutr.* 109:1168-1174, Monoglyceryl Acetoacetate: A Ketone Body-carbohydrate Substrate For Parenteral Feeding Of The Rat (1979). According to Birkhahn and Border, elevated levels of ketone bodies were thus achieved without any detrimental side effects in the test subjects. The authors concluded from the observations that monoacetoacetin was providing energy to the rat. In this study, the ketone bodies were being utilized for their ability to spare protein. No mention was made of the potential for monoacetoacetin to provide ketone bodies to provide energy for the brain and to address conditions associated with reduced neuronal glucose metabolism.

In WO 95/09146 (Eastman Chemical; Medical College of Ohio), the use of bisacetoacetin (the ester corresponding to 1 mole of glycerin and 2 moles of acetoacetate) for parenteral nutrition was described. Bisacetoacetin was infused into patients at a level corresponding to 8-9.3 g/Kg body weight/day to affect hyperketonemia. No detrimental side effects were said to be observed. In this study, the ketone bodies were being utilized for their ability to spare protein. No mention was made of the potential for diacetoacetin to provide ketone bodies as an alternative energy source for the brain to address conditions associated with reduced neuronal glucose metabolism.

U.S. Pat. No. 5,093,044 (Kabivitrum AB) generally describes the use of triacetoacetin as a nutrient for animals and humans. In the reported studies, rats allegedly tolerated triacetoacetin at the amount of 10 g/Kg body weight/day. In these studies, the ketone bodies were being utilized for their ability to spare protein. No mention was made of the potential for triacetoacetin to provide ketone bodies as an alternative energy source for the brain to address conditions associated with reduced neuronal glucose metabolism.

U.S. Pat. No. 6,380,244 (Metabolix, Inc.) describes the use of oligomers of 3-hydroxyalkanoic acids for providing ketone bodies to the body. The reference does not disclose the use of glyceride esters.

WO 95/09144 (Eastman Chemical; Medical College of Ohio) generally describes the use of 1-(DL-3-hydroxybutyryl)-glycerol in parenteral nutrition to replace glucose. It does not discuss the treatment of conditions associated with reduced neuronal glucose metabolism through the use of glyceride esters. In the described rat feeding studies, it was observed that both 1-(DL-3-hydroxybutyryl)-glycerol and DL-tris-(3-hydroxybutyrl)-glycerol were not acutely toxic and did not show any indication of chronic toxicity.

Tieu et al (2003) have observed that direct administration of 3-hydroxybutyrate can protect mice against a neurotoxin known to induce Parkinson's disease. Tieu et al., D-β-Hydroxybutyrate rescues mitochondrial respiration and mitigates features of Parkinson disease, *J. Clin. Invest.* 112:892-901 (2003). No mention in the reference, however, was made of the potential to use glyceride esters of 3-hydroxybutyrate or as an alternative energy source for neuronal glucose metabolism disorders.

The present technology provides a readily utilized alternative source of energy for the brain and other tissues of a human or animal in the form of glyceride esters of ketone bodies. The present technology also provides one or more compositions useful in the treatment or prevention of neuronal glucose metabolism diseases and/or disorders.

BRIEF SUMMARY OF THE INVENTION

[Not Applicable]

BRIEF DESCRIPTION OF SEVERAL VIEWS OF THE DRAWINGS

[Not Applicable]

DETAILED DESCRIPTION OF THE INVENTION

The present technology provides alternative sources of ketone bodies that are both physiologically and organoleptically acceptable to a human or animal body. They can be employed to achieve the desired effects of a ketogenic diet used to mitigate the symptoms of Parkinson's disease, amyotrophic lateral sclerosis (ALS, also called Lou Gehrig's disease), Alzheimer's disease, Huntington's disease, epilepsy and other diseases or disorders characterized by impaired glucose metabolism. The alternative sources of ketone bodies include mono-, di- and triglyceride esters of acetoacetate and mixtures thereof, and/or mono-, di- and triglyceride esters of 3-hydroxybutyrate and mixtures thereof. These glyceride esters can be administered orally as a dietary supplement or in a nutritional composition.

In accordance with at least one embodiment of the present technology, a glyceride ester of acetoacetate or 3-hydroxybutyrate or a mixture thereof can be orally administered to a patient to reduce or eliminate the symptoms of diseases associated with reduced or impaired neuronal glucose metabolism. The glyceride ester suitable for the present technology can be mono-, di- and triglyceride esters, or a mixture thereof. For example, the glyceride ester can be selected from the group consisting of mono-, di- and triglyceride esters of acetoacetate, mono-, di- and triglyceride esters of 3-hydroxybutyrate, and mixtures thereof. Although not wanting to be bound by any particular theory, it is believed that a higher triacetoacetin content can lead to more acid functionality per dosage. In a preferred embodiment, for example, the glyceride esters of the present technology can contain about 75% by weight or more of triglyceride esters.

Optionally, the glyceride esters of acetoacetate or 3-hydroxybutyrate of the present technology can contain fatty acid moieties derived from oils of vegetable, fish, animal, or single-celled organisms. Such oils may contain Omega-6 fatty acids, Omega-3 fatty acids, medium chain fatty acids, and/or conjugated fatty acids. Although not wanting to be bound by any particular theory, it is believed that Omega-3 fatty acids and conjugated Omega-6 fatty acids can provide "heart-healthy" therapeutic activity to a human or animal, while the medium chain fatty acids can aid in ketone formation and can be metabolized like sugars.

The glyceride esters of the presently described technology can be provided in the form of dietary supplements and/or nutritional compositions. It should be understood by those skilled in the art that such nutritional supplements or nutritional compositions of the present technology can be formulated utilizing conventional means. The dietary supplements or nutritional compositions can be made to any form suitable for administration to human bodies or animals. For example, oral administration of the glyceride esters of the present technology can be in the form of capsules, pills, liquids, tablets, edible bars, drinks, gels, thin films, or gums.

Further, at least one daily dosage of the glyceride esters of the present technology can be an effective amount to reduce or eliminate the symptoms of the disease(s) associated with reduced or impaired neuronal glucose metabolism of the person or animal being treated. For example, the glyceride esters of the present technology can be administered in a daily dosage of from about 6 to about 10 g.

In accordance with at least one other embodiment of the present technology, the dietary supplement or nutritional composition of the present technology can comprise a glyceride ester of (1) acetoacetate and/or 3-hydroxybutyrate and (2) a fatty acid moiety derived from oils of vegetable, fish, animal, or single-celled organisms, or mixtures thereof.

The glyceride ester of the present technology can be produced by any available technology. For example, it can be produced by esterification, transesterification, or interesterification of a glycerol and/or glyceryl ester with a fatty acid or fatty acid derivative. The fatty acid or derivative thereof can be acetoacetic or 3-hydroxybutyric, and can be derived from vegetable, fish, animal, or single-celled organisms, or a mixture thereof. For example, the fatty acid can be an Omega-6 fatty acid, Omega-3 fatty acid, a medium chain fatty acid, a conjugated fatty acid, or a mixture thereof.

The esterification, transesterification, or interesterification can be performed using either chemical or enzymatic catalysis.

Suitable chemical catalysts include, for example, hydroxides, carbonates, bicarbonates, and alkoxide salts of alkali, alkaline earth and transition metals. Examples of alkali or alkaline earth metals include, but are not limited to, sodium, lithium, potassium, magnesium, calcium, barium, iron, zinc and copper. When a chemical catalyst is used, the reaction is preferably carried out at a temperature of from about 90° C. to about 200° C., alternatively from about 120° C. to about 190° C., alternatively from about 140° C. to about 180° C.

Suitable enzymatic catalysts include, for example, *Candida antarctica, Candida rugosa, Aspergillus oryzae, Rhizomucor miehei, Thermomyces lanuginosa, Pseudomonas cepacia, Pseudomonas fluorescens, Rhizopus delemar* and *Pseudomonas sp* lipases. When enzymatic catalysis is used, the reaction can be carried out at a temperature of from about 30° C. to about 75° C., alternatively from about 35° C. to about 55° C., with or without a solvent. The solvent can be, for example, hexane, heptane, acetone, ethyl acetoacetate, or the like.

To make a triglyceride of acetoacetin in accordance with at least one embodiment of the present technology, glycerol can be treated with tert-butyl acetoacetate at a temperature of from about 110° C. to about 120° C., alternatively from about 60° C. to about 180° C., for approximately 14 to 21 hours, alternatively 3 to 21 hours. The reaction is preferably provided in an inert (e.g., nitrogen) atmosphere. During the reaction, tert-butyl alcohol by-product can be removed, for example, via distillation. At the end of the reaction, the remaining tert-butyl acetoacetate can be removed through distillation (e.g., at about 59 to about 75° C., 1 mmHg). The product obtained may be deodorized, for example, by the addition of water under vacuum (e.g., 1 mmHg) at a temperature range of from about 50° C. to about 80° C. The structure can be confirmed through, for example nuclear magnetic resonance (NMR), elemental analyses (C,H,N) and/or gas chromatography (GC).

In accordance with at least one other embodiment of the present technology, glycerol can be treated with ethyl acetoacetate in presence of a lipase at from about 55° C. to about 70° C., alternatively from about 20 to about 75, for approximately 14 to 48 hours, alternatively 20 to 36 hours. The lipase can be, for example, Novozyme® 435, Lipozyme® RM IM, or Lipozyme® TL IM, all available from Novozymes A/S, Franklinton, N.C. The reaction can be performed in an inert (e.g., nitrogen) atmosphere. During the reaction, ethyl alcohol by-product can be removed, for example, via distillation. At the end of the reaction, the remaining ethyl acetoacetate can be removed through distillation (e.g., at 60° C., 1 mmHg). The structure of the triglyceride of acetoacetin produced can be confirmed through, for example, NMR analysis and/or GC.

Although not wanting to be bound by any particular theory, it is believed that triglyceride of acetocetin exists in tautomeric forms, which include the keto (acetoacetate) and enol (3-hydroxybutyl-2-enoate) tautomers. These tautomers can exist in equilibrium with each other.

To make a structured lipid of acetoacetate and an oil in accordance with at least one further embodiment of the present technology, any kind of oil (e.g., a vegetable or fish oil) can be reacted with ethyl acetoacetate in the presence of a lipase (e.g., Novozyme® 435, Lipozyme® RM IM, or Lipozyme® TL IM) at from about 55° C. to about 70° C., alternatively from about 20 to about 75, for approximately 14 to 48 hours, alternatively 20 to 36 hours. The structure of the resulting product can be confirmed by, for example, GC analysis.

In accordance with at least another embodiment of the present technology, an oil (e.g., a vegetable or fish oil, or medium chain triglycerides "MCTs") can be reacted with a triglyceride of acetoacetin in the presence of a lipase (e.g., Novozyme® 435, Lipozyme® RM IM, or Lipozyme® TL IM) at from about 55° C. to 70° C., alternatively from about 20 to about 75, for approximately 14 to 48 hours, alternatively 20 to 36 hours. The structure of the structured lipid produced can be confirmed by, for example, GC analysis.

The presently described technology and its advantages will be better understood by reference to the following examples. These examples are provided to describe specific embodiments of the present technology. By providing these specific examples, the applicants do not limit the scope and spirit of the present technology. To the contrary, it will be understood by those skilled in the art that the full scope of the presently described technology encompasses the subject matter defined by the claims appending this specification, and any alterations, modifications, or equivalents of those claims.

EXAMPLES

Materials

Glycerin (99+% by weight) was purchased from ACROS Organics (New Jersey, USA). Tert-butyl acetoacetate (99%) was purchased from Eastman (Kingsport, Tenn.) or from ACROS Organics. Ethyl acetoacetate (99% by weight) was purchased from ACROS Organics. Novozyme 435 lipase and Lipozyme TL-IM lipase were purchased from Novozymes (Franklinton, N.C.).

Equipment

Reactions were conducted in 4-neck round bottom flasks with condenser and receiver, using a mechanical stirrer with a heating manual, temperature controller and a nitrogen sparge.

Example 1

Preparation of Triacetoacetin

A mixture of glycerin (70.4 g, 0.765 mole) and tert-butyl acetoacetate (483.65 g, 3.061 mole) was heated to about 115° C. and maintained for approximately 21 hours. Reaction was performed under nitrogen. Tert-butyl alcohol produced was removed during the process. The remaining tert-butyl acetoacetate was removed through distillation (1 mmHg, 80°

C.). Following distillation, a pale yellow liquid was obtained and determined to be 96.6% triglyceride triacetoacetin and 3.4% diglyceride diacetoacetin. The composition was confirmed by NMR, Elemental Analyses (C,H,N) and GC.

Example 2

Preparation of Triacetoacetin Using a Lipase

A mixture of glycerin (5 g, 0.054 mole), ethyl acetoacetate (70 g, 0.54 mole) and Novozyme 435 (3 g) was heated to about 55° C. and maintained for approximately 14 hours. Ethyl acetoacetate was treated as both a solvent and a reactant. This reaction was kept under nitrogen atmosphere. The remaining ethyl acetoacetate was removed through distillation (1 mmHg, 60° C.). The resulting pale yellow liquid was analyzed as 94.4% triglyceride triacetoacetin and 5.6% diglyceride diacetoacetin. The product also contained ethyl isomers in addition to acetoacetate and 3-hydroxybut-2-enoate. The resultant composition was confirmed by NMR and GC.

Example 3

Preparation of Structured Lipid of Acetoacetin and Safflower Oil

A solution of high linoleic safflower oil (59 g, 0.066 mole), ethyl acetoacetate (43 g, 0.33 mole) and lipase (Novozyme 435, 6 g) was heated to about 55° C. and kept in that temperature for approximately seven (7) hours. Subsequently another portion of ethyl acetoacetate (10 g, 0.077 mole) was added, and reaction was provided for approximately an additional seven (7) hours. The process was maintained under nitrogen atmosphere. The resultant composition was then analyzed by GC, and the mixed glycerides containing acids from both the safflower oil and acetoacetate were observed.

Example 4

Preparation of Structured Lipid from Acetoacetic and a Medium Chain Triglyceride A mixture of ethyl acetoacetate (1 mol) and caprylic/capric methyl esters (2 moles) was stirred with glycerin (1 mol) and lipase (Novozyme 435, 2.5% wt) at about 65° C. for approximately 48 hours. A nitrogen sparge was provided throughout the reaction to aid in the removal of ethanol and methanol. The product was deodorized (at 80° C., 11 mmHg) to remove residual alcohols. Water was introduced into a heated reaction mix (80° C.) under reduced pressure (30 mm Hg) over an approximately 30 minute period. The composition was confirmed by GC.

Example 5

Preparation of Structured Lipid from Triacetoacetin and Fish Oil

An equimolar mixture of triacetoacetin (as prepared in Examples 1 and 2 above) and fish oil was stirred with a lipase (Lipozyme TL-IM) at about 55° C. for approximately 48 hours under a nitrogen atmosphere. The composition was then confirmed by GC.

We claim:

1. A method to reduce or eliminate symptoms of a disease or disorder associated with reduced neuronal glucose metabolism comprising the step of administering to a human or animal a therapeutically effective amount of at least one glyceride ester of 3-hydroxybutyrate.

2. The method of claim 1, wherein the disease or disorder associated with reduced neuronal glucose metabolism is Parkinson's disease, Alzheimer's disease, amyotrophic lateral sclerosis, Huntington's Disease, or epilepsy.

3. The method of claim 1, wherein the glyceride ester comprises a mono-, di- or triglyceride ester of 3-hydroxybutyrate.

4. The method of claim 1, wherein the glyceride ester comprises a fatty acid moiety derived from an oil of a vegetable, a fish, an animal or a single-celled organism, or a mixture thereof.

5. The method of claim 4, wherein the oil comprises an Omega-6 fatty acid, an Omega-3 fatty acid, a medium chain fatty acid, a conjugated fatty acid, or a mixture thereof.

6. The method of claim 1, wherein the glyceride ester is provided in the form of a dietary supplement or a nutritional composition.

7. The method of claim 6, wherein the dietary supplement or nutritional composition is in the form of a capsule, a pill, a liquid, a tablet, an edible bar, a drink, a gel, a thin film, or a gum.

8. A composition for reducing or eliminating symptoms of a disease or disorder associated with reduced neuronal glucose metabolism, comprising at least one structured glyceride ester of 3-hydroxybutyrate, and a fatty acid moiety derived from fish oil.

9. The composition of claim 8, wherein the fish oil comprises an Omega-3 fatty acid, a medium chain fatty acid, or a mixture thereof.

10. The composition of claim 8, wherein the composition is in the form of a capsule, a pill, a liquid, a tablet, an edible bar, a drink, a gel, a thin film, or a gum.

11. A process to make a composition for reducing or eliminating symptoms of a disease or disorder associated with reduced neuronal glucose metabolism, comprising the step of esterifying, transesterifying, or interesterifying a glycerol, a glyceryl ester, or a mixture thereof with a an Omega-3 fatty acid, a derivative thereof, or a mixture thereof.

12. A composition for reducing or eliminating symptoms of a disease or disorder associated with reduced neuronal glucose metabolism produced by the process of claim 11.

* * * * *